United States Patent [19]

Ross et al.

[11] 4,261,926

[45] Apr. 14, 1981

[54] REDUCTIVE ALKYLATION OF SUBSTITUTED ANILINES

[75] Inventors: Lawrence J. Ross, Martinsville; Stephen D. Levy, Trenton, both of N.J.

[73] Assignee: American Cyanamid Company, Stamford, Conn.

[21] Appl. No.: 95,811

[22] Filed: Nov. 19, 1979

Related U.S. Application Data

[63] Continuation-in-part of Ser. No. 840,195, Oct. 7, 1977, abandoned, which is a continuation-in-part of Ser. No. 710,998, Aug. 2, 1976, abandoned, which is a continuation-in-part of Ser. No. 563,045, Mar. 28, 1975, abandoned, which is a continuation-in-part of Ser. No. 373,078, Jun. 25, 1973, abandoned.

[51] Int. Cl.$^3$ .............................................. C07C 85/08
[52] U.S. Cl. .................................. 564/305; 564/423; 564/440; 564/442; 564/443

[58] Field of Search ........... 260/574, 576, 577, 583 R, 260/585 C, 573

[56] References Cited

U.S. PATENT DOCUMENTS

| | | | |
|---|---|---|---|
| 2,213,204 | 9/1940 | Carleton | 260/576 |
| 2,947,784 | 8/1960 | Martin et al. | 260/577 |
| 3,450,764 | 6/1969 | Altwicker | 260/571 |
| 3,522,309 | 7/1970 | Kirby | 260/577 |
| 3,541,153 | 11/1970 | Sandridge | 260/577 |

*Primary Examiner*—John Doll
*Attorney, Agent, or Firm*—H. G. Jackson

[57] ABSTRACT

N-alkylated aromatic amines are produced by reductively alkylating an aromatic amine with pressurized hydrogen in the presence of a ketone, a noble metal catalyst and a promoter acid having a pKa between 0.3 and 1.5.

9 Claims, No Drawings

REDUCTIVE ALKYLATION OF SUBSTITUTED ANILINES

This is a continuation in part of copending application Ser. No. 840,195, filed Oct. 7, 1977, now abandoned which is a continuation-in-part of application Ser. No. 710,998, filed Aug. 2, 1976, now abandoned which in turn is a continuation-in-part of application Ser. No. 563,045, filed Mar. 28, 1975, now abandoned which in turn is a continuation-in-part of application Ser. No. 373,078, filed June 25, 1973, now abandoned.

This invention relates to certain novel reductive alkylation reactions for the preparation of certain substituted N-alkylated aromatic amines which are desirable as intermediates in the preparation of 3,4-disubstituted-2,6-dinitroaniline herbicides by the method described in copending patent application Ser. No. 565,885, filed Apr. 7, 1975.

The N-alkylated aromatic amines produced by the process of the present invention have the formula:

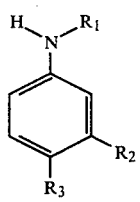
(I)

wherein $R_1$ is cycloalkyl $C_3-C_6$, secondary alkyl $C_3-C_6$ optionally monosubstituted with $C_1-C_4$ alkoxy group; $R_2$ represents hydrogen, halogen, alkoxy $C_1-C_4$, alkyl $C_1-C_4$ and monosubstituted alkyl $C_1-C_4$ wherein the substituent is fluorine or alkoxy $C_1-C_4$; and wherein $R_3$ represents hydrogen, alkyl $C-C_4$, alkoxy $C_1-C_4$, trifluoromethyl, methylsulfonyl or halogen.

Illustrative alkyl $C_1-C_4$ substituents are methyl, ethyl, n-propyl, iso-propyl, n-butyl, t-butyl, sec-butyl, and the like. The cycloalkyls include cyclopropyl, -butyl, -hexyl, etc.

Illustrative secondary alkyl $C_3-C_8$ substituents are 2-propyl, 2-butyl, 3-pentyl, 3-methyl-2-butyl, 2-heptyl, 2-octyl and the like.

Illustrative monosubstituted alkyl substituents including the secondary monosubstituted alkyl substituents are 4-methoxy-2-butyl, 2-ethoxybutyl and the like.

Illustrative compounds of formula I which may be produced by the process of the present invention include, for example:
N-2-butyl-3,4-dimethylaniline;
N-3-pentyl-3,4-dimethylaniline;
N-2-propyl-3,4-dimethylaniline;
N-2-butyl-3-methyl-4-t-butylaniline;
N-3-pentyl-3-methyl-4-chloroaniline;
N-3-pentyl-3-methyl-4-trifluoromethylaniline;
N-2-hexyl-3,4-dimethylaniline;
N-3-pentyl-3-methoxymethyl-4-methylaniline;
N-3-pentyl-3-methoxymethyl-4-trifluoromethylaniline;
N-2-butyl-4-bromo-3-methylaniline;
N-2-pentyl-4-bromo-3-methylaniline;
N-2-hexyl-4-chloro-3-methylaniline; and
N-2-pentyl-3-ethoxy-4-methylaniline.

The N-alkylated aromatic amines are produced by reacting the corresponding aromatic amine with the appropriate ketone, a noble metal catalyst and an acid having a pKa value ranging from 0.3 to 1.5, and preferably ranging from 0.5 to 1.0. The pKa value is defined as the negative logarithm to the base 10 of the first ionization constant of the acid in water.

The aromatic amines used in the process of the present invention have the formula:

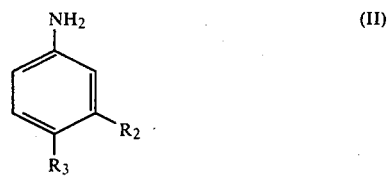
(II)

wherein $R_2$ and $R_3$ are as defined for formula I above.

Illustrative amines include, for example, 3,4-xylidine, 3,4-diethylaniline, 3,4-di-n-butylaniline, 3-methyl-4-ethylaniline, 3-methyl-4-trifluoromethylaniline, 3-methyl-4-chloroaniline, 3-ethyl-4-bromoaniline, 3-methoxymethyl-4-methylaniline and the like.

The amines may be reacted directly with the ketone or their oxidized precursors may be employed to indirectly produce the N-alkylated aromatic amine. Illustrative oxidized precursors to the formula II aromatic amines include the nitro, nitroso, hydrazo, azo, azoxy, hydroxylamine, diazonium salt or Schiff's base compound corresponding thereto.

Illustrative acids include, for example, 2-naphthalenesulfonic acid, p-toluenesulfonic acid, ethylbenzene-sulfonic acid, trichloroacetic acid, and the like.

The ketone is selected to correspond with the N-alkyl group desired. For example, if a 2-propyl substituent is desired as $R_1$, one would employ dimethyl ketone.

Stated in greater detail, the ketones employed herein may be represented by formulas IV and VI below.

For those N-alkylated aromatic amines of the formula:

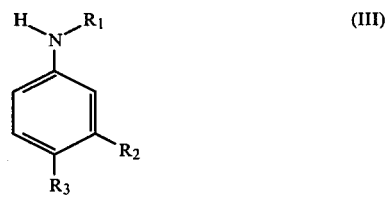
(III)

wherein $R_1$ represents secondary alkyl $C_3-C_7$, and $R_2$ and $R_3$ are as defined for formula I above, one would employ the following ketone:

(IV)

wherein $R_4$ and $R_5$ are lower alkyl $C_1-C_5$ provided that the total number of carbon atoms in $R_4$ plus $R_5$ does not exceed six, thereby insuring a carbon atom range of from $C_3$ to $C_7$ in $R_1$.

Where it is desired to produce an N-alkylated aromatic amine of the formula:

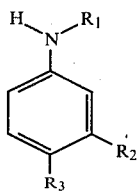

wherein $R_1$ represents a secondary monosubstituted alkyl $C_3$–$C_4$ wherein the substituent is an alkoxy $C_1$–$C_4$ and $R_2$ and $R_3$ are as defined for formula I above, one would employ a ketone of the formula:

(IV)

wherein $R_6$ and $R_7$ are lower alkyl $C_1$–$C_2$ provided the total carbon content of $R_6$ plus $R_7$ does not exceed $C_3$ and $R_6$ or $R_7$ is monosubstituted with a $C_1$–$C_4$ alkoxy group.

Illustrative ketones that may be used in the process of this invention include, for example, acetone, 2-butanone, 2-pentanone, 3-pentanone, 2-hexanone, 3-hexanone, 2-heptanone, 3-heptanone, 4-heptanone, 1-methoxy-3-pentanone, ethoxy-2-propanone, methyl isobutyl ketone, and the like.

The noble metal catalysts used are those conventionally used in hydrogenation reactions, that is, members of Group VIII of the Periodic Table in the platinum and palladium families. They are preferably in finely divided form absorbed or supported on a suitable substrate. Platinum and palladium are preferred catalysts. Platinum on a carbon support is most preferred by reason of the fact that it is readily available from commercial sources and its use avoids conversions of the ketone to the corresponding carbinol which will occassionally occur where palladium is employed. Yields of 85.5% or higher are afforded thereby.

A typical procedure for practicing the reductive alkylation of this invention is as follows. A pressure reactor is charged with the aromatic amine or an oxidized precursor thereof, the appropriate ketone, the acid promoter and noble metal catalyst. The reactor is then preferably deoxygenated by evacuation followed by purging with purified nitrogen. The reactor is then pressurized to 10 to 80 psi (gauge) with hydrogen gas and the reaction mixture heated to effect reaction. Higher pressures (e.g. to 120 psig) may be used if desired, their use being limited only by the equipment employed. Temperatures in the range of 40° C. to 150° C. are generally suitable, with temperatures ranging from 60° C. to 125° C. being most preferred. The advantages of these pressures and temperatures are that any well-stirred commercial reactor may be used without recourse to heavy-walled autoclaves. Reaction periods of from 10 minutes to several hours, during which time the pressure in the reactor is either maintained, if desired, by repressurizing with hydrogen gas or allowed to decrease, are generally sufficient to insure completion or reaction. The reaction times are generally limited by the ability to add hydrogen quickly enough, especially when large reactors (1000–2000 gallon capacity) are used. Thereafter, the reaction mixture is permitted to cool, the reactor is vented and opened, and the contents removed. The desired product is worked up in a conventional manner.

Satisfactory results may be achieved when the amount of acid used in the promoter system is as low as 0.1 mole per hundred moles of the amine or its oxidized precursor. The upper limit of acid is only limited by practical considerations. The most preferable amount of acid used ranges from 1 to 3 moles of acid per hundred moles of amine or its oxidized precursor.

The noble metal catalyst is preferably used in an amount which is not less than about 0.3 gram of noble metal (preferably platinum) per mole of the amine or amine precursor being alkylated. If the catalyst is adsorbed on a substrate, adjustments should be made in the amount of material used so that at least an amount of about 0.3 gram of metal per mole of the amine or its precursors is present, notwithstanding the quantity of the substrate on which it is adsorbed.

The amount of metal typically found in commercial catalysts ranges from 1% to 50% based on the weight of the support. A preferred commercial catalyst contains 5% platinum on carbon which is used in an amount of about 5% of the amine either present in the reaction mixture or formed from the oxidized precursor.

The catalyst used in the process of this invention can be recycled in a conventional manner, but it is preferable to fortify the spent catalyst with sufficient fresh catalyst to maintain its level of activity. The amount of fresh catalyst added is normally less than 10% of the original usage and is preferably 2% to 5% of this usage.

The catalyst can be pre-reduced or one can utilize the noble metal oxide and reduce it to the metal in the reaction mixture.

The ketone and aromatic amine combine on an equimolar basis. A single mole of hydrogen is consumed in conversion of the amine to the corresponding N-alkylated compound. Where an oxidified precursor is employed in lieu of the amine, additional hydrogen will be required in the reduction of the precursor. The mole ratio of ketone to amine is from about 1.1:1 to 10:1 and preferably 1.1:1 to 2.2:1.

The hydrogen is usually employed at a level in excess of that required for the conversion. It is preferably employed in sufficient quantity to maintain a pressure of about 10 pounds per square inch (psi), with pressures of from about 40 to 80 psi being most preferred.

As mentioned above, the N-alkylated aromatic amines produced by the process of the present invention are useful as intermediates in the manufacture of the corresponding 2,6-dinitroaniline herbicides and bud growth regulators of Belgian Pat. Nos. 787,939 and 785,584.

Accordingly, the invention relates to a method for the manufacture of an N-alkylated aromatic amine of Formula I by reacting an aromatic amine of Formula II with a noble metal catalyst and the appropriate ketones and promoter acids and is further characterized by the step of forming an aromatic amine in situ by reduction of an oxidized precursor thereof; or, a method wherein said precursor is the nitro, nitroso, azo or azoxy derivative of said aromatic amine. In the latter case it further relates to the manufacture of N-sec-butyl-3,4-xylidine wherein the starting mixture comprises 4-nitro-o-xylene and methyl ethyl ketone; or, to the manufacture of N-3-pentyl-3,4-xylidine which comprises reacting a starting mixture comprising 4-nitro-o-xylene and diethyl ketone, wherein the mole ratio of diethyl ketone to 4-nitro-o-xylene ranges from 1.1:1 to 2.2:1, with hydrogen gas under a pressure of 30-60 psi and a temperature of 60° C. to 80° C. in the presence of a platinum metal catalyst adsorbed on carbon and 1 to 3 mole percent of 2-naphthalenesulfonic acid, based on 4-nitro-o-xylene, until the reaction is completed, separating the platinum catalyst from the reaction mixture and recovering N-3-pentyl-3,4-xylidine therefrom.

It further relates to said method wherein the reaction is conducted in a pressure vessel under hydrogen gas at a pressure ranging from 10 psi to 80 psi and at a temperature ranging from 40° C. to 120° C., wherein the mole ratio of ketone to starting compound ranges from 1.1:1 to 10:1, wherein the promoter acid is an aromatic sulfonic acid based on starting compound ranges from 0.1 to 10 mole percent, wherein the metal catalyst is platinum, and wherein the mole percent of platinum metal to starting compound ranges from 0.005:1 to 0.25:1: or, wherein the pressure of hydrogen gas ranges from 40 psi to 70 psi and the temperature ranges from 60° C. to 100° C., wherein the mole ratio of ketone to starting compound ranges from 1.1:1 to 2.2:1, wherein the mole ratio of aromatic sulfonic acid to starting compound ranges from 0.02:1 to 0.03:1, and wherein the mole ratio of platinum metal to starting compound ranges from about 0.05:1 to 0.15:1; or, where the starting mixture comprises a mixture of 3,4-xylidine and diethyl ketone manufacturing N-3-pentyl-3,4-xylidine.

It further relates to a method for the manufacture of N-3-pentyl-α,α,α-trifluoro-p-toluidine which comprises reacting a mixture of α,α,α-trifluoro-p-toluidine and diethyl ketone, wherein the mole ratio of diethyl ketone to α,α,α-trifluoro-p-toluidine ranges from 1.1:1 to 2.2:1, with hydrogen gas under a pressure of 30-60 psi and at a temperature of 50° C. to 80° C. in the presence of a platinum metal catalyst adsorbed on carbon and 1 to 3 mole percent of 2-naphthalenesulfonic acid, based on α,α,α-trifluoro-p-toluidine, until the reaction is completed, separating the platinum catalyst from the reaction mixture and recovering N-3-pentyl-α,α,α-trifluoro-p-toluidine therefrom; and to a method for the manufacture of N-(2-butyl)-4-t-butylaniline which comprises reacting a mixture of p-t-butylnitrobenzene and methyl ethyl ketone, wherein the mole ratio of methyl ethyl ketone to p-t-butylnitrobenzene ranges from 1.1:1 to 2.2:1, with hydrogen gas under a pressure of 30 psi to 80 psi and at a temperature of 50° C. to 80° C. in the presence of a platinum metal catalyst adsorbed on carbon and 1 to 3 mole percent of 2-naphthalenesulfonic acid, based on N-(2-butyl)-4-t-butylaniline, until the reaction is completed, separating the platinum catalyst therefrom and recovering N-(2-butyl)-4-t-butylaniline therefrom.

This invention is primarily further described by the reductive alkylation of 4-nitro-o-xylene and 3,4-xylidine in the examples, but it is to be understood that any of the amines or their oxidized precursors may be substituted therefor. In each case the parts and percentages used herein are by weight unless otherwise indicated.

EXAMPLE 1

Amounts of 24.2 g. (0.20 mole) of 3,4-xylidine, 38.4 g (0.44 mole) of diethyl ketone, 1.2 g. of 5% platinum on carbon, and 0.90 g (2 mole percent) of 2-naphthalenesulfonic acid were charged to an autoclave and the autoclave was sealed, evacuated, purged with nitrogen and then pressurized with hydrogen gas to 47 psi. The temperature of the contents of the autoclave was raised to 60° C. and held at 60° C. to 65° C. for about ¾ of an hour and then lowered to about 25° C. The autoclave was vented, opened and the contents withdrawn and filtered to separate the catalyst. The lower layer of the filtrate was separated in a separatory funnel and the catalyst cake, filter flask and separatory funnel were rinsed with 10 ml. of diethyl ketone which was combined with the organic phase and evaporated to a constant weight of 38.2 g. This material was 97.2% pure, corresponding to 37.1 g of product or to a 97.2% of product yield (the theoretically obtainable maximum weight of 0.2 mole of product is 38.2 g, hence in the present example the percent purity and percent yield are the same).

EXAMPLE 2

A Parr reaction bottle was charged with 24.2 grams of 3,4-xylidine (0.2 mole), 0.9 gram of 2-naphthalenesulfonic acid, 1.2 grams of 5% platinum on carbon and 38.0 grams of cyclohexanone (0.388 mole). The mixture was reacted with hydrogen at 70° C. under hydrogen pressure of 38-60 psig. The formation of a single reaction product was verified by gas-liquid chromatography. This product was purified by distillation, and its identity as N-cyclohexyl-3,4-xylidine was verified by I.R. and N.M.R. spectroscopy. The distillation gave 45.3 g of the above material, found to be 80.4% pure by G.C. corresponding to 36.4 g of product, or to a yield of 90.1%.

EXAMPLE 3

To a Parr reaction bottle there was charged 24.2 grams (0.2 mole) of 3,4-xylidine, 1.2 grams of 5% platinum on carbon, 28 grams diethyl ketone and 0.46 gram of trifluoroacetic acid (pKa about 0.3). The mixture was hydrogenated at 70° C. and a hydrogen pressure of 42-60 psig. The reaction was stopped after 110% of the theoretical hydrogen was consumed.

The desired product, N-3-pentylxylidine was produced in an amount of 38.0 g, analyzing 89.4% pure. Thus the product weight was 34.0 g, corresponding to a yield of 88.9%.

EXAMPLE 4

To a Parr reaction bottle was charged 24.2 grams of 3,4-xylidine, 28 grams of diethyl ketone 0.516 grams of dichloroacetic acid (pKa about 1.5) and 1.2 grams of 5% platinum on carbon. Forty minutes at 70° C. and hydrogen pressure of 44-60 psig were required to consume 100% of the theoretical amount of hydrogen. A yield of 38.8 g of N-3-pentyl-3,4-xylidine, analyzing 93.9% pure, was obtained. Thus 36.4 g of product was obtained, corresponding to a yield of 95.4%.

EXAMPLE 5

3,4-Xylidine (24.2 grams; 0.2 mole), 2-heptanone (50.2 grams, 0.44 mole), 2-naphthalenesulfonic acid (0.9 g) and 5% of platinum on carbon (1.2 gms) were charged to a Parr reaction bottle and treated with hydrogen at 70° C. and a hydrogen pressure of 41-60 psig. The theoretical amount of hydrogen was consumed within 15 minutes. The mixture was held an additional 35 minutes, producing 43.6 g of N-2-heptyl-3,4-xylidine. The above sample analyzed 100% pure, corresponding to a yield of 99%.

EXAMPLE 6

Amounts of 24.2 g 3,4-xylidine, 1.20 g of 5% platinum on carbon, 38.4 g diethyl ketone and 0.2 ml (equivalent to 2 mole percent) of concentrated $H_2SO_4$ were charged to an autoclave. The atmosphere was replaced by hydrogen after evacuating via a vacuum source. The mixture was pressurized with 50 psi hydrogen and heated at 59°–69° C. for 65 minutes. The autoclave was vented, the product filtered, and the lower aqueous phase removed. The organic phase was concentrated using a rotary vacuum evaporator to give 35.8 gms of material containing 70.1% of N-3-pentyl-3,4-xylidine. The yield of this desired product was 65.7%.

EXAMPLE 7

Amounts of 24.2 g 3,4-xylidine, 1.20 g of 5% platinum on carbon, 38.4 g diethyl ketone and 0.41 g of concentrated hydrochloric acid (equivalent to 2 mole percent) were charged to an autoclave. The atmosphere was replaced by hydrogen after evacuating via a vacuum source. The mixture was pressurized with 50 psi hydrogen and heated at 60°–69° C. for 25 minutes. The autoclave was vented, the product filtered, and the lower aqueous phase removed. The organic phase was concentrated using a rotary vacuum evaporator to give 37.8 gms of material containing 77.4% of N-3-pentyl-3,4-xylidine. The yield of this desired product was 70.5%.

EXAMPLE 8

A Parr hydrogenation apparatus was charged with 1.2 grams 5% platinum on carbon, 0.62 g 3,5-dihydroxybenzoic acid (pKa=1.92), 24.2 grams 3,4-xylidine and 28.0 grams diethyl ketone. The mixture heated to 70° C. and hydrogenated at 35-60 psig. The mixture was cooled, filtered, the filter cake washed with methanol, and the organic phase (87.7 g) analyzed by gas-liquid chromatography. Thus, 28.7 g of N-3-pentyl-3,4-xylidine was obtained, corresponding to a yield of 75.1%.

EXAMPLE 9

Amounts of 24.2 g (0.20 mole) of 3,4-xylidine 38.4 g (0.44 mole) of diethyl ketone, 1.2 g of 5% platinum on carbon, and 0.26 g (2 mole %) of glacial acetic acid were charged to an autoclave and the autoclave was sealed, evacuated, purged with hydrogen and then pressurized with hydrogen to 50 psi. The temperature of the autoclave was raised to 60° C. and held at 60°–68° C. for 0.9 hours (very little, if any, hydrogen was being absorbed at this point). The autoclave was vented and the product filtered to separate the catalyst. The lower, aqueous phase, of the filtrate was separated and the upper, organic phase, was evaporated to constant weight of 35.0 g. Analysis of the residue showed it to be 78.8% pure, corresponding to 28.7 g of N-3-pentyl-3,4-xylidine (72.2% yield).

EXAMPLE 10

Amounts of 24.2 g of 3,4-xylidine, 38.4 g of diethyl ketone, 0.6 g of 10% platinum on carbon, 0.2 g (1.7 mole %) glacial acetic acid and 10 g of water were charged to an autoclave. The autoclave was evacuated and the atmosphere replaced with 50 psi of hydrogen. The autoclave was heated and held at 60°–64° C. for 3 hours: the theoretical amount of hydrogen was absorbed after 2.3 hours. The autoclave was cooled and vented. The lower aqueous phase was removed after the mixture was neutralized with 10 ml of 5% sodium carbonate solution. The organic phase, after evaporation in vacuo of volatiles gave 32.7 g of oil containing 71.7% of N-3-pentyl-3,4-xylidine which is equivalent to a yield of 61.5%.

EXAMPLE 11

Amounts of 24.2 g 3,4-xylidine, 38 g diethyl ketone, 1.2 g of 5% platinum on carbon and 0.83 g α-naphthalenesulfonic acid were charged to an autoclave and the atmosphere replaced with hydrogen. The mixture was pressurized to 60 psi with hydrogen and heated at approximately 60°–70° C. for two hours. The mixture was cooled, vented and filtered. The lower aqueous phase was removed and the organic phase concentrated in vacuo. The product weighed 38.5 g and contained, by analysis, 97.2% N-3-pentyl-3,4-xylidine which is equivalent to a yield of 98%.

EXAMPLES 12–15

In these examples the use of various promoter acids were evaluated. The general procedure employed was the same as in Example 1. The data obtained in these examples are summed up in Table I below, along with the data obtained in Examples 1 to 11. In all cases the mole percent of acid used was based on 100 moles of 3,4-xylidine. The starting materials were diethyl ketone, cyclohexanone or 2-heptanone, and 3,4-xylidine. Diethyl ketone is used in all examples excepting where otherwise stated to the contrary and noted by superscripts. With the exception of Example 10, fresh 5% platinum on carbon catalyst was used in the examples. In example 10, fresh 10% platinum on carbon catalyst was used. These results show that acids having pKa values of 0.3 to 1.5 produce good, i.e. 85.5% to 99.0%, yields of product in short reaction times under relatively mild conditions of temperature and pressure. They also show that acids having a pKa value above and/or below the critical pKa range produce, at best, a 75.1% yield of product.

TABLE I

Reductive Alkylation of 3,4-Xylidine

| Example | Ketone (m) / Xylidine (m) | Acid | pKa | Mole % Acid | Platinum Catalyst (g) / Xylidine (m) | Temp. °C. | Pressure psi. | Hours to completion | Crude product weight in g | % Purity of crude product | Product weight in g | % yield of product |
|---|---|---|---|---|---|---|---|---|---|---|---|---|
| 3 | 1.63 | CF$_3$CO$_2$H | 0.3 | 2.0 | 6.0 | 70 | 42–60 | 0.6 | 38.0 | 89.4 | 34.0 | 88.9 |
| 1 | 2.2 | β-naphthalene-sulfonic acid | 0.57 | 2.0 | 6.0 | 60–65 | 47 | 0.45 | 38.2 | 97.2 | 37.1 | 97.2 |
| 2 | 1.9[1] | β-naphthalene-sulfonic acid | 0.57 | 2.0 | 6.0 | 70 | 38–60 | 1.0 | 45.3 | 80.4* | 36.4** | 90.1** |
| 5 | 2.2[2] | β-naphthalene-sulfonic acid | 0.57 | 2.0 | 6.0 | 70 | 41–60 | 0.8 | 43.6 | 100.0* | 43.6** | 99.0** |
| 11 | 1.63 | α-naphthalene-sulfonic acid | 0.68 | 2.0 | 6.0 | 70 | 44–60 | 2.0 | 38.5 | 97.2 | 37.4 | 98.0 |
| 12 | 2.2 | Cl$_3$CCO$_2$H | 0.7 | 2.0 | 6.0 | 66–70 | 50–34 | 0.3 | 37.7 | 90.1 | 34.0 | 88.9 |
| 13 | 2.2 | benzene-sulfonic acid | 0.7 | 2.0 | 6.0 | 58–65 | 46–28 | 0.5 | 37.7 | 95.9 | 36.2 | 94.6 |

TABLE I-continued

Reductive Alkylation of 3,4-Xylidine

| Example | Ketone (m)/Xylidine (m) | Acid | pKa | Mole % Acid | Platinum Catalyst (g)/Xylidine (m) | Temp. °C. | Pressure psi. | Hours to completion | Crude product weight in g | % Purity of crude product | Product weight in g | % yield of product |
|---------|---|---|---|---|---|---|---|---|---|---|---|---|
| 14 | 2.2 | p-toluene-sulfonic acid | 0.9 | 2.0 | 6.0 | 59–70 | 50–32 | 0.3 | 36.8 | 88.8 | 32.7 | 85.5 |
| 15 | 2.2 | p-ethylbenzene-sulfonic acid | 0.9 | 2.0 | 6.0 | 60–67 | 50–32 | 0.4 | 41.6 | 88.8 | 36.9 | 96.7 |
| 4 | 1.63 | $Cl_2CHCO_2H$ | 1.5 | 2.0 | 6.0 | 70 | 44–60 | 0.7 | 38.8 | 93.9 | 36.4 | 95.4 |
| 6 | 2.2 | $H_2SO_4$ | 0.0 | 2.0 | 6.0 | 59–60 | 50–32 | 1.0 | 35.8 | 70.1 | 25.1 | 65.7 |
| 7 | 2.2 | HCl | 0.0 | 2.0 | 6.0 | 60–69 | 50–32 | 0.3 | 34.8 | 77.4 | 26.9 | 70.5 |
| 8 | 1.63 | 3,5-dihydroxy-benzoic acid | 1.92 | 2.0 | 6.0 | 70 | 35–60 | 2.0 | 87.7 | 32.7 | 28.7 | 75.1 |
| 9 | 2.2 | Acetic acid | 4.75 | 2.2 | 6.0 | 60–68 | 50–34 | 0.9 | 35.0 | 78.8 | 27.6 | 72.2 |
| 10 | 2.2 | Aqueous acetic acid | 4.75 | 1.7 | 3.0[3] | 61–64 | 50–32 | 2.3 | 32.7 | 71.7 | 23.4 | 61.5 |

β-naphthalenesulfonic acid = 2-naphthalenesulfonic acid
[1] = cyclohexanone
[2] = 2-heptanone
[3] = 10% platinum on carbon
* = % estimate, based on G.C. analysis
** = derived from % estimate (*)

EXAMPLES 16–21

The following examples illustrate the use of p-toluenesulfonic acid as the promoter acid resulting in excellent yields and enabling the catalyst to be repeatedly recycled. The general procedures employed were the same as that used in Example 1 starting with diethyl ketone and 3,4-xylidine under the reaction conditions and results noted in Table II.

TABLE II

Reductive Alkylation of 3,4-xylidine using Recycled Catalyst

| Example | Ketone (m)/Xylidine (m) | Mole % Acid | Catalyst (g)/Xylidine (m) | No. of Recycles | Temp. °C. | Pressure psi | Hours to completion | Crude product weight in g | % Purity of crude product | Product weight in g | % yield of product |
|---------|---|---|---|---|---|---|---|---|---|---|---|
| 16 | 2.2 | 2.0 | 3.0[a] | 0 | 63–71 | 50–32 | 0.3 | 38.8 | 87.6 | 34.0 | 89.0 |
| 17 | 2.2 | 2.0 | 3.0[a] | 1 | 61–69 | 50–32 | 0.3 | 37.9 | 92.6 | 35.1 | 91.9 |
| 18 | 2.2 | 2.0 | 3.0[a] | 2 | 60–68 | 50–32 | 0.4 | 38.2 | 93.4 | 35.7 | 93.4 |
| 19 | 2.2 | 2.0 | 3.0[a] | 3 | 61–66 | 50–32 | 0.5 | 38.2 | 94.4 | 36.1 | 94.4 |
| 20 | 2.2 | 2.0 | 3.0[a] | 4 | 59–62 | 50–34 | 2.5 | 38.9 | 98.0 | 38.1 | 99.8 |
| 21 | 2.2 | 2.0 | 3.0[b] | 5 | 59–62 | 50–33 | 0.9 | 39.2 | 96.0 | 37.6 | 98.5 |

[a] = Catalyst was 10% platinum on carbon
[b] = Catalyst was fortified with 0.12 grams of fresh 10% platinum on carbon

EXAMPLE 22

To a pressure vessel was charged 8.05 grams (0.05 mole) of α,α,α-trifluoro-p-toluidine, 6.9 grams (0.08 mole) of diethyl ketone, 0.3 gram of 5% platinum on carbon and 0.23 gram of 2-naphthalenesulfonic acid. The vessel was closed and the reaction mixture was heated to 55° C. to 60° C.; hydrogen gas was then introduced to a pressure level of from 45 to 50 psi. The mixture was allowed to react until the hydrogen uptake ceased. It was then cooled to room temperature and the vessel was vented. The mixture was removed from the vessel, filtered and the lower water layer was removed from the filtrate. The filtrate was evaporated under vacuum to obtain 11.2 grams of the desired product as an oil (97% of theory). The identity of the product was verified using proton magnetic resonance spectroscopy and by elemental analysis which showed a nitrogen content of 5.92% which corresponds to a theoretical value of 6.06%.

EXAMPLE 23

Amounts of 18.0 grams of p-t-butyl-nitrobenzene (0.1 mole), 13.6 grams of methyl ethyl ketone (0.22 mole), 0.6 gram of 5% platinum on carbon and 0.46 gram of 2-naphthalenesulfonic acid monohydrate were added to a 500 ml. pressure reactor and the reactor was closed. The reactor was pressurized with hydrogen gas and hydrogenated at from 60° C. to 75° C. until about 6% more than the theoretical amount of hydrogen was consumed. The system was then cooled to room temperature, vented, and the contents removed therefrom and filtered. The lower layer of the filtrate was discarded and the upper layer was concentrated in vacuo to obtain 20.7 grams of the desired product as a crude material (a yield of about 100% of theory). The product was identified by its infrared absorption spectrum which was identical to that of an analytically pure sample of N-(2-butyl)-4-t-butylaniline.

EXAMPLE 24

Amounts of 28.3 grams of 3-chloro-p-toluidine (0.2 mole), 23.0 grams of methyl ethyl ketone (0.32 mole), 1.2 grams of 5% platinum on carbon, and 0.9 gram of 2-naphthalenesulfonic acid were charged to a 500 ml. pressure reactor and the reactor was closed. The reactor was pressurized with hydrogen gas to a pressure of about 51 psi and the temperature was raised to from 40° C. to 65° C. and maintained until the drop in pressure indicated that the theoretical amount of hydrogen was consumed. The system was then cooled to room temperature, vented and the contents removed therefrom. The lower water layer was discarded and the upper concentrated in vacuo to obtain the desired product as a crude material in a 100.1% yield. Comparison of the crude material by infrared and nuclear magnetic resonance spectroscopy to pure N-(2-butyl)-3-chloro-p-toluidine verified its structure and demonstrated that it was contaminated with less than 5% of mthyl ethyl ketone and a small quantity of 2-naphthalenesulfonic acid.

EXAMPLE 25

To a Parr reaction bottle was charged 11.2 grams of cyclobutanone, 12.1 grams of 3,4-xylidine, 0.45 grams of 2-naphthalenesulfonic acid and 0.6 grams of 5% platinum on carbon. The reaction bottle was pressurized with hydrogen gas to a pressure of about 60 psig and the temperature was raised to 70° C. and maintained until the drop in pressure indicated that the theoretical amount of hydrogen was consumed. The system was then cooled to room temperature, vented and the contents removed therefrom. The catalyst was filtered off and the organic phase was concentrated in vacuo to obtain 17.0 g of crude product (97% crude yield). The crude was vacuum distilled. The desired product was collected in a fraction boiling at 160° C. to 175° C. under 0.9 mm pressure. Verification of the product as N-cyclobutyl-3,4-xylidine was effected by the N.M.R. spectrum. The product has a mass number of 175.

EXAMPLE 26

A mixture of 151 grams (1.0 mole) 4-nitro-o-xylene, 138 grams (1.6 moles) diethyl ketone, 5.8 grams of 5% platinum on carbon and 3.7 grams of 2-naphthalenesulfonic acid monohydrate were added to a pressure vessel. Hydrogen was fed into the reactor at a pressure of 30–40 psi and a temperature of 80°–100° C. When hydrogen uptake ceased, the vessel was cooled and vented. After filtering the catalyst, the aqueous phase was separated and the upper layer concentrated in vacuo to give 191 grams of 96% pure N-(1-ethylpropyl)-3,4-xylidine (96% yield).

EXAMPLE 27

A mixture of 151.2 grams (1.0 mole) 4-nitro-o-xylene, 161 grams (2.2 moles) methyl ethyl ketone, 6 grams of 5% platinum on carbon and 4.5 g of 2-nahthalenesulfonic acid monohydrate were added to a pressure vessel. Hydrogen was fed into the pressure vessel at a pressure of 20 psig. When hydrogen uptake ceased (in about 2 hours), the vessel was vented and the reaction mixture filtered. The phases were separated and the organic phase was concentrated in vacuo (at 20 mm and 70° C.) to give 178.8 g of 96.4% pure N-(sec-butyl)-3,4-xylidine in a yield of 97.2%.

EXAMPLE 28

Following the procedure of Example 1, but substituting methyl ethyl ketone for diethyl ketone, under a hydrogen gas pressure range of 30 psig to 50 psig, a temperature range of 60° C. to 70° C., and using (as desired) 0.45 g to 1.35 g (1 to 3 mole percent) of 2-naphthalenesulfonic acid, N-(sec-butyl)-3,4-xylidine is obtained.

We claim:
1. A method for the manufacture of an N-alkylated aromatic amine of the formula:

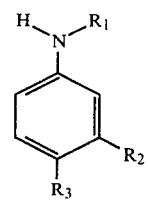

wherein $R_1$ is cycloalkyl $C_3$–$C_6$, secondary alkyl $C_3$–$C_6$ unsubstituted or monosubstituted with a $C_1$–$C_4$ alkoxy group; $R_2$ represents hydrogen, halogen, alkoxy $C_1$–$C_4$, alkyl $C_1$–$C_4$, or monosubstituted alkyl $C_1$–$C_4$ wherein the substituent is fluorine or alkoxy $C_1$–$C_4$; and wherein $R_3$ represents hydrogen, alkyl $C_1$–$C_4$, alkoxy $C_1$–$C_4$, trifluoromethyl, methylsulfonyl, or halogen, by reacting an aromatic amine of the formula:

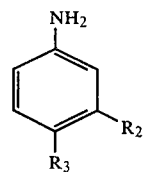

wherein $R_2$ and $R_3$ are as defined hereinabove, with hydrogen a platinum catalyst, a promoter acid and a ketone, the improvement characterized in the use therewith of a promoter acid having a pKa between 0.3 and 1.5 wherein the reaction is conducted in a pressure vessel under hydrogen gas at a pressure ranging from 10 psi to 80 psi and at a temperature ranging from 40° C. to 120° C., wherein the mole ratio of ketone to starting compound ranges from 1.1:1 to 10:1, wherein the promoter acid is an aromatic sulfonic acid, wherein the mole percent of aromatic sulfonic acid based on starting compound ranges from 0.1 to 10 mole percent, and wherein the mole percent of platinum metal to starting compound ranges from 0.005:1 to 0.25:1.

2. A method according to claim 1 wherein the pressure of hydrogen gas ranges from 40 psi to 70 psi and the temperature ranges from 60° C. to 100° C., wherein the mole ratio of ketone to starting compound ranges from 1.1:1 to 2.2:1, wherein the mole ratio of aromatic sulfonic acid to starting compound ranges from 0.02:1 to 0.03:1, and wherein the mole percent of platinum metal to starting compound ranges from about 0.05:1 to 0.15:1.

3. A method according to claim 1 further characterized by the step of forming the aromatic amine in situ by reduction of a oxidized precursor thereof.

4. A method according to claim 3 wherein said precursor is the nitro, nitroso, azo or azoxy derivative of said aromatic amine.

5. A method for the manufacture of N-sec-butyl-3,4-xylidine according to claim 4 wherein the starting mixture comprises 4-nitro-o-xylene and methyl ethyl ketone.

6. A method for the manufacture of N-3-pentyl-3,4-xylidine according to claim 4 which comprises reacting a starting mixture comprising 4-nitro-o-xylene and diethyl ketone, wherein the mole ratio of diethyl ketone to 4-nitro-o-xylene ranges from 1.1:1 to 2.2:1, with hydrogen gas under pressure of 30 psi to 60 psi and a temperature of 60° C. to 80° C. in the presence of a platinum metal catalyst adsorbed on carbon and 1 to 3 mole percent of 2-naphthalenesulfonic acid, based on 4-nitro-o-xylene, until the reaction is completed, separating the platinum catalyst from the reaction mixture and recovering N-3-pentyl-3,4-xylidine therefrom.

7. A method for the manufacture of N-3-pentyl-3,4-xylidine according to claim 1, wherein the starting mixture comprises a mixture of 3,4-xylidine and diethyl ketone.

8. A method for the manufacture of N-3-pentyl-$\alpha,\alpha,\alpha$-trifluoro-p-toluidine according to claim 1 which comprises reacting a mixture of $\alpha,\alpha,\alpha$-trifluoro-p-toluidine and diethyl ketone, wherein the mole ratio of diethyl ketone to $\alpha,\alpha,\alpha$-trifluoro-p-toluidine ranges from 1.1:1 to 2.2:1, with hydrogen gas under a pressure of 30 psi to 60 psi and at a temperature of 50° C. to 80° C. in the presence of a platinum metal catalyst adsorbed on carbon and 1 to 3 mole percent of 2-naphthalenesulfonic acid, based on $\alpha,\alpha,\alpha$-trifluoro-p-toluidine, until the reaction is completed, separating the platinum catalyst from the reaction mixture and recovering N-3-pentyl-$\alpha,\alpha,\alpha$-trifluoro-p-toluidine therefrom.

9. A method for the manufacture of N-(2-butyl)-4-t-butylaniline according to claim 4 which comprises reacting a mixture of p-t-butylnitrobenzene and methyl ethyl ketone, wherein the mole ratio of methyl ethyl ketone to p-t-butyl-nitrobenzene ranges from 1.1:1 to 2.2:1, with hydrogen gas under a pressure of 30 psi to 80 psi and at a temperature of 50° C. to 80° C. in the presence of a platinum metal catalyst adsorbed on carbon and 1 to 3 mole percent of 2-naphthalenesulfonic acid, based on N-(2-butyl)-4-t-butylaniline, until the reaction is completed, separating the platinum catalyst therefrom and recovering N-(2-butyl)-4-t-butyl-aniline therefrom.

* * * * *